(12) United States Patent
Bombardelli et al.

(10) Patent No.: US 6,607,757 B2
(45) Date of Patent: *Aug. 19, 2003

(54) SOYA EXTRACT, PROCESS FOR ITS PREPARATION AND PHARMACEUTICAL COMPOSITION

(75) Inventors: Ezio Bombardelli, Milan (IT); Bruno Gabetta, Milan (IT)

(73) Assignee: Indena S.p.A., Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 09/902,226

(22) Filed: Jul. 11, 2001

(65) Prior Publication Data

US 2002/0058062 A1 May 16, 2002

Related U.S. Application Data

(60) Division of application No. 09/492,921, filed on Jan. 28, 2000, now Pat. No. 6,280,777, which is a continuation-in-part of application No. PCT/EP98/04770, filed on Jul. 30, 1998.

(30) Foreign Application Priority Data

| Jul. 30, 1997 | (DE) | ......................................... 197 32 855 |
| Jul. 30, 1997 | (DE) | ......................................... 197 32 822 |
| Jul. 30, 1997 | (DE) | ......................................... 197 32 866 |

(51) Int. Cl.$^7$ ............................................. A61K 35/78
(52) U.S. Cl. ...................................................... 424/757
(58) Field of Search ....................... 424/757, 58; 514/2, 514/811, 899

(56) References Cited

U.S. PATENT DOCUMENTS

| 4,428,876 A | 1/1984 | Iwamura |
| 4,501,734 A | 2/1985 | Tanaka et al. |
| 5,141,746 A | 8/1992 | Fleury et al. |
| 5,624,910 A | 4/1997 | Vallee et al. |
| 6,020,471 A | 2/2000 | Johns et al. |
| 6,280,777 B1 * | 8/2001 | Bombardelli et al. |

FOREIGN PATENT DOCUMENTS

| DE | 3400258 | 6/1986 |
| JP | 59088064 | 5/1984 |
| JP | 62005917 | 1/1987 |
| JP | 63245648 | 10/1988 |
| JP | 4036242 | 2/1992 |
| JP | 6136225 | 5/1994 |
| JP | 7173148 | 7/1995 |
| JP | 8291191 | 11/1996 |
| WO | WO 93/23069 | 11/1993 |
| WO | WO96/10341 | 4/1996 |
| WO | WO96/35441 | 11/1996 |
| WO | WO96/36332 | 11/1996 |

OTHER PUBLICATIONS

Messina M. et al., "The Role of Soy Products in Reducing Risk of Cancer," J. National Cancer Institute, vol. 83, n. 8, pp. 541–546 (1991).
Okubo K. et al., "Soybean Saponin and Isoflavonoids," 1994 ACS Symposium, Ser. 546, pp. 330–339 (1994).
Cassidy A., "Physiological Effects of Phyto–oestrogens in Relation to Cancer and Other Human Health Risks," Proceedings of the Nutrition Society, vol. 55, pp. 399–417 (1996).
Shutt D.A. et al., "Steroid and Phyto–Oestrogen Binding to Sheep Uterine Receptors In Vitro," J. Endocrinology, vol. 52, pp. 299–310 (1972).
Nomura A. et al., "Breast Cancer and Diet Among the Japanese in Hawaii," The American Journal of Clinical Nutrition, vol. 31, pp. 2020–2025 (1978).
Hirayama T., "Diet, Nutrition and Cancer," Japan Scientific Societies Press, pp. 41–53 (1986).
Severson R.K. et al., "A Prospective Study of Demographics, Diet, and Prostate Cancer Among Men of Japanese Ancestry in Hawaii," Cancer Research, vol. 49, pp. 1857–1860 (1989).
Konoshima, T., et al., "Anti–tumor Promotong Activities of Afromosin and Soyasaponin I Isolated from *Wistaria Brachybotrys*," J. Natural Products, vol. 55, No. 12, 1776–1778, Dec. 1992.

* cited by examiner

*Primary Examiner*—Christopher R. Tate
*Assistant Examiner*—Michele C. Flood
(74) *Attorney, Agent, or Firm*—Pennie & Edmonds LLP

(57) ABSTRACT

A soya extract having a content of glucoside isoflavones of at least 13% by weight and a content of 0.6 to 1.5 parts by weight of group B soya saponins per 1 part by weight of glucoside isoflavones. Also, pharmaceutical compositions containing this extract and methods of administering the extract to treat conditions such as pre- or post-menopausal symptoms, cancer, such as breast or prostrate cancer, or alcoholism. The extracts are made by a process which includes the steps of treating ripe whole soya beans or oil-free soya flour with an aliphatic alcohol to obtain a first extract; concentrating the first extract to form a concentrated first extract; purifying the concentrated first extract by treatment with at least one aliphatic hydrocarbon; and extracting active components from the purified concentrated first extract with a water-immiscible aliphatic alcohol to obtain a second extract. Preferably, the final extract is concentrated and dried to form the desired soya extract.

4 Claims, 1 Drawing Sheet

SOYA EXTRACT, PROCESS FOR ITS PREPARATION AND PHARMACEUTICAL COMPOSITION

This is a divisional of application Ser. No. 09/492,921, filed Jan. 28, 2000 now U.S. Pat. No. 6,280,777, which is a continuation-in-part of PCT application PCT/EP98/04770 filed on Jul. 30, 1998, the content of which is expressly incorporated herein by reference thereto.

BACKGROUND OF THE INVENTION

The invention relates to novel extracts obtained by extraction of ripe complete soya beans or from oil-free soya flour (Glycine max (L.) MERRIL, Leguminosae family), their production and formulations containing these extracts. The novel extracts are characterized by their content of isoflavones and saponins in defined ratios.

It is known that soya contains saponin and isoflavone components in addition to saccharide and amino acid components, as well as proteins and mineral salts in amounts which depend on their geographical origin and the conditions under which the plant was cultivated and harvested.

The saponin contents have been divided into three classes depending on the chemical structure of their triterpene components: soya saponins of groups A, B and E (Okubo K. et al., ACS Symp., Ser. 546, 330, 1994).

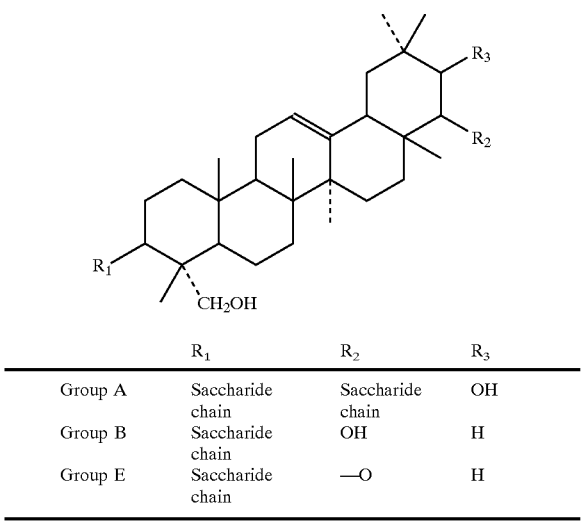

| | $R_1$ | $R_2$ | $R_3$ |
|---|---|---|---|
| Group A | Saccharide chain | Saccharide chain | OH |
| Group B | Saccharide chain | OH | H |
| Group E | Saccharide chain | —O | H |

Isoflavone components consist of glucoside isoflavones (daidzin, genistin and glycitin) which can contain acyl radicals, e.g. malonyl radicals, linked to the saccharide chain.

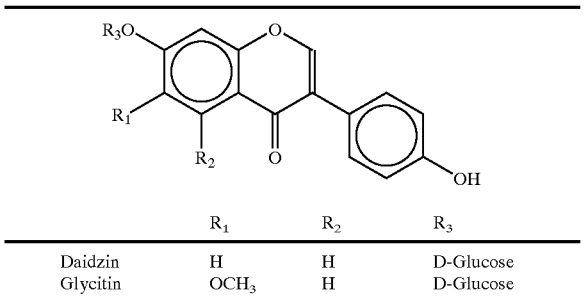

| | $R_1$ | $R_2$ | $R_3$ |
|---|---|---|---|
| Daidzin | H | H | D-Glucose |
| Glycitin | $OCH_3$ | H | D-Glucose |

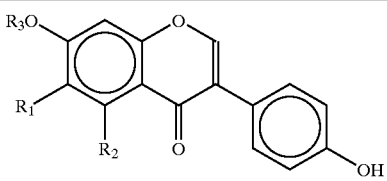

| | $R_1$ | $R_2$ | $R_3$ |
|---|---|---|---|
| Genistin | H | OH | D-Glucose |
| Daizdein | H | H | H |
| Glycitein | $OCH_3$ | H | H |
| Genistein | H | OH | H |

According to biomedical literature and epidemiological information published in recent years, principally in relation to populations of the East, which consume soya-based foods to a great extent, the use of these foods to a high degree reduces pre-menopausal and post-menopausal symptoms in women (A. Cassidy, Proceedings of the Nutrition Society, 1996, 55, 339–417). These facts, which still lack a clear scientific basis, are usually ascribed to the isoflavone aglycones genistein, daidzein and glycitein, which are present in the various soya-based foods.

Isoflavones are usually considered to be plant oestrogens, and numerous in-vitro studies have shown that these substances act in a mechanism competing with mammalian oestrogens with an activity which is rated lower by a factor of 500 to 1000 than that of oestradiol (D. A. Shutt and R. I. Cox, Journal of Endocrinology, 1972, 52, 299–310).

According to further biomedical literature and epidemiological information published in recent years, principally relating to population groups in the East, which consume soya-based foods to a great extent, the use of these foods decreases to a high degree breast cancer in women and cancer of the prostate in men (A. Nomura, B. E., Henderson J. Lee, American Journal of Clinical Nutrition, 1978, 31, 2020–2025; T. Hirayama in Diet, Nutrition and Cancer, 1986 pp. 41–53, Y. Hayashi, M. Nagao, T. Sugimura, S. Takayama, L. Tomatis, L. W. Wattenberg and G. N. Wogan eds. Tokyo: Japanese Scientific Society Press; R. K. Severson, A. M. Y. Nomura, J. S. Grove, G. N. Stemmerman, Cancer Research, 1989, 49,1857–1860). Also, these facts, which still lack a clear scientific basis, are usually ascribed to the isoflavone aglycones genistein, daidzein and glycitein which are present in the various soya-based foods.

These isoflavones have been studied in in-vitro models with regard to their capacity to interact with protein kinases, in particular with tyrosine kinase, enzymes which appear to play a role in proliferation of tumour cells.

Numerous attempts have been made recently to prepare drugs based on soya extracts for the preventive treatment of pre-menopausal and post-menopausal symptoms and also for the preventive treatment of cancer. Some patents or patent applications describe compositions of novel soya extracts obtained by chemical or enzymatic hydrolysis of the glucoside isoflavones present in soya beans or soya bean sprouts (Kikkoman Corp. J-08291191; Kikkoman Corp J-07173148; Kelly GE WO-9323069; Kikkoman Corp. J-0511707566). All of these publications are concerned solely with the preparation of isoflavones of high concentration and activities with regard to the control of pre-menopausal and post-menopausal disorders and to antitumour activity.

It has now been found, that in contrast to that described previously, extracts which contain glucoside isoflavones and group B soya saponins in defined ratios are considerably more active than isoflavones alone as regards both, the prevention or treatment of pre-menopausal and post-menopausal symptoms and the prevention or treatment of cancer.

A further aspect related to the extract of the invention is concerned with alcohol abuse and alcohol dependency or alcohol addicition. These are phenomena which can be summarized under the term "alcoholism" and form a serious problem of the entire modern society (Gessa G. L., "Bisogno compulsive di bere e principio del piacere" [The compulsion to drink and the pleasure principle] in Medicina delle tossicodipendenze [Medicine of drug dependency] II, 5 (1994)). In Italy, for example, more than 9% of the population (about 5 million) are heavy drinkers and more than 1 million are alcohol-dependent (Calamo-Specchia F. P., "Epidemiologia dell'alcolismo in Italia" [Epidemiology of alcoholism in Italy] in Atti del VII Congresso Nazionale della S.I.A. [Reports of the 7th National Congress of the S.I.A.] Mediserve, Rome, 295–301 (1991)). These numbers are increased when countries such as the USA are taken into account, where more than 13 million are alcohol-dependent. Alcohol abuse and actual alcohol dependency lead to very high public expenditure (since 1991, in the USA about 200 billion dollars per year have been consumed) and are causes of great social and psychological damage to those affected.

Existing attempts to treat alcoholism in addition to those of a psychological nature (group therapy etc.) consist of applying drugs such as disulfiram and calcium carbamide, which act on alcohol metabolism, hepatic aldehyde dehydrogenase being inhibited and therefore the emetic acetaldehyde level being increased, together with all the unwanted phenomena which occur in the course of alcohol intake.

According to the prior art, the only plants whose derivatives were used for treating alcoholism are *Pueraria lobata* (*Radix puerarie*) and *Salvia miltiorrhiza*, which are very widely used in traditional Chinese medicine and form the subject-matter of the Patent Applications WO 93/00896 and WO 96/35441. In addition to the use of the extracts, these patent applications claim the use of pure substances such as daidzein and its semisynthetic derivatives in WO 93/00896, or diterpenoids, such as tanshinone and miltirone in WO 96/35441. An effect on alcohol dehydrogenase with the occurrence of the above-described side effect has been disclosed for the isoflavone derivatives, while the same mechanism has been excluded for the diterpenoid compounds. Furthermore, Patent Application WO 96/36332 disclosed the effect of forskolin in the reduction of alcohol consumption.

In addition to the above mentioned prior art WO 96/10341 discloses food or health products comprising substantially pure hypocotyls of soya seeds. No reference is made to the extraction procedure and to the ratio between isoflavones and saponins according to the present invention.

U.S. Pat. No. 4,428,876 discloses a process for isolating saponins and flavonoids from leguminous plants. The there disclosed extraction of soybean with 0.4% aqueous sodium hydroxide makes the final extract different from that of the present invention. Again, no reference is made to the ratio between isoflavones and saponins according to the present invention.

JP 59088064 is directed to the isolation and the use of saponins only. The same applies to DE 34 DO 258. Similarly JP 61036225 is directed to the isolation and purification of saponins and JP 62005917 to the preparation of pure saponins completely free of isoflavones. JP 4036242 concerns the preparation of pure saponin or of an extract having a high saponin/isoflavone ratio as an antiinflammatory compound.

EP-A-426 998 discloses the preparation of isoflavones from soybean and in particular of genistine and daidzine malonate. No reference is made to the extraction of saponins and to the ratio between isoflavones and saponins.

JP 63245648 is directed to the preparation of soybean food material devoid of saponins and isoflavones which are considered harshness components rendering the food unedible.

Mark Messina et al., Journal of the National Cancer Institute, Vol. 83, No. 8, Apr. 17, 1991, pages 541–546 is directed to the role of soy products in reducing risk of cancer already reported in scientific literature. Neither this document nor other literature, however, refer to an extract containing-saponins and isoflavones in the ratio of this invention, let alone the pharmacological effect obtainable by such a specific extract.

SUMMARY OF THE INVENTION

Suprisingly, it has now been found that extracts containing glucoside isoflavones and group B soya saponins in defined ratios can be used with success to reduce deliberate alcohol consumption. These extracts are significantly more effective than the isoflavones alone and act via a mechanism which is different from that of the inhibition of alcohol dehydrogenase, since the plasma alcohol level remains unchanged.

Thus, the invention relates to a soya extract having a content of glucoside isoflavones of at least 13% by weight and a content of 0.6 to 1.5 parts by weight of group B soya saponins per 1 part by weight of glucoside isoflavones. Preferably, the content of group B soya saponins is 1 part by weight per 1 part by weight of glucoside isoflavones.

The invention also relates to a pharmaceutical composition containing, as an active component, one of these soya extracts and a pharmaceutically acceptable carrier or diluent.

Another embodiment of the invention relates to methods for treating various conditions, such as pre- or post-menopausal symptoms in a female subject, cancer, such as breast cancer in a female subject or prostate cancer in a male subject, or alcoholism. The method step includes administering to a subject in need of such treatment a therapeutically effective amount of one of these soya extracts.

Yet another embodiment of the invention relates to a process for producing these soya extracts. This process comprises the steps of treating ripe whole soya beans or oil-free soya flour with an aliphatic alcohol to obtain a first extract; concentrating the first extract to form a concentrated first extract; purifying the concentrated first extract by treatment with at least one aliphatic hydrocarbon; and extracting active components from the purified concentrated first extract with a water-immiscible aliphatic alcohol to obtain a second extract.

Preferably, the process further comprises concentrating the second extract followed by drying to form the desired soya extract. Advantageously, the process further comprises adsorbing the second extract from the concentrated first extract to a polystyrene-based adsorption resin, flushing the resin with water, and eluting the second extract with ethanol. Additional preferred steps include suspending the first extract in a mixture of a water-miscible alcohol and water and diluting it with a water-immiscible aphotic solvent; heating the resulting mixture to complete dissolution and then holding it at room temperature to allow precipitation of group B soya saponins in a solution that contains an organic phase and an aqueous phase; collecting the precipitated group B soya saponins by filtration of the solution; separating the organic phase from the water phase, and then concentrating the organic phase and drying it to produce isoflavone components; and mixing the collected group B soya saponins with the isoflavone components to form the desired soya extract.

DETAILED DESCRIPTION OF THE PREFERRED EMBODIMENTS

Figure 1:
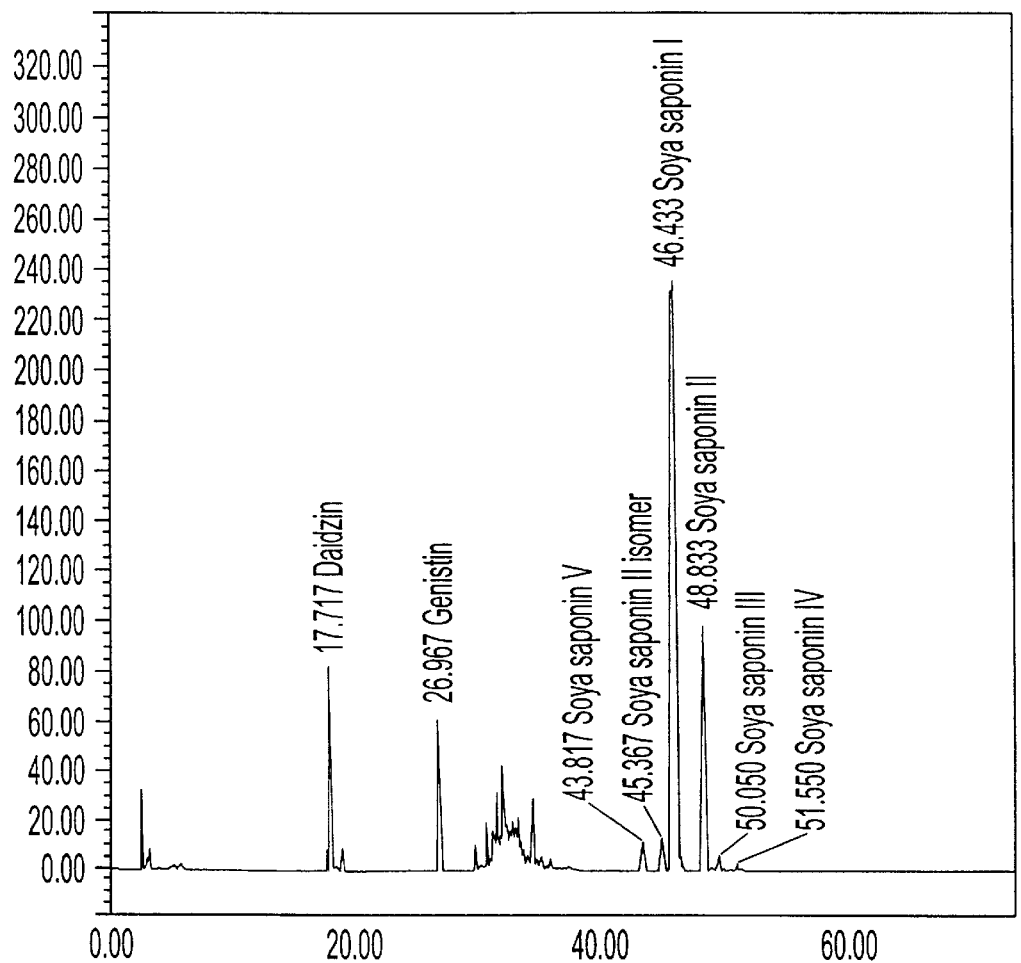
FIG. 1 is an HPLC diagram of an extract obtained by the process of Example 1.

As shown by HPLC-MS analysis, the group B soya saponins which have a beneficial effect on the activity of the isoflavone components have the following structures:

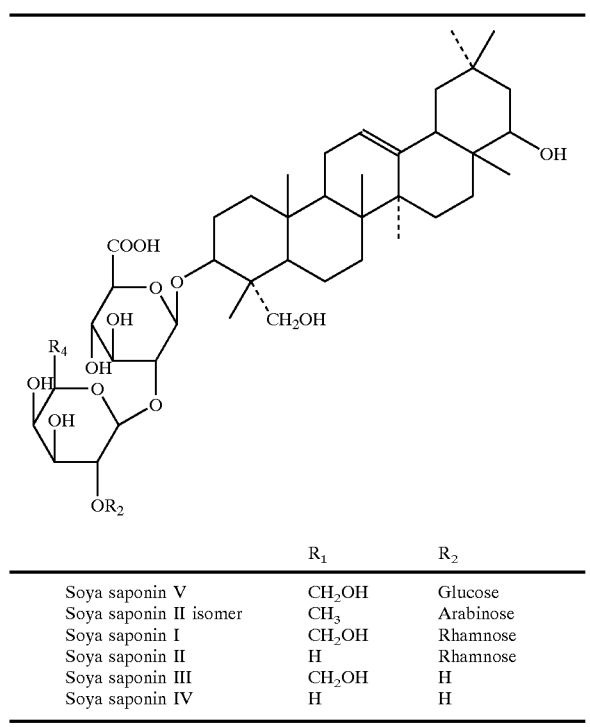

|  | $R_1$ | $R_2$ |
| --- | --- | --- |
| Soya saponin V | $CH_2OH$ | Glucose |
| Soya saponin II isomer | $CH_3$ | Arabinose |
| Soya saponin I | $CH_2OH$ | Rhamnose |
| Soya saponin II | H | Rhamnose |
| Soya saponin III | $CH_2OH$ | H |
| Soya saponin IV | H | H |

The invention further relates to a process for producing the above-defined extract, which is characterized in that it comprises the following stages:
a) the extraction of ripe whole soya beans or oil-free soya flour with aliphatic alcohols or a mixture of these alcohols with water;
b) concentration of the extract from stage a);
c) purification of the concentrated extract of stage b) from oily and lipophilic substances by treatment with aliphatic hydrocarbons;
d) extraction of the active components with water-immiscible aliphatic alcohols;
e) concentration of the extract from stage d) and its drying.

In particular, the extracts according to the invention can be produced by extracting ripe whole soya beans or oil-free soya flour containing group B soya saponins and glucoside isoflavones in the reciprocal ratio of 3:2 to 2:3 with aliphatic alcohols alone or in a mixture with water—preferably with a mixture of ethanol/water, such as 95% pure ethanol. After concentration of the extract and purification of oily and lipophilic substances by treatment with aliphatic hydrocarbons (e.g. n-hexane or n-heptane), the active components are extracted with water-immiscible aliphatic alcohols such as n-butanol, isobutanol and isoamyl alcohol. After concentration to a reduced volume, the organic phase is dried under reduced pressure. The invention further relates to a modification of the above process, in which, after stage b) or c), the concentrated alcohol extract is subjected to the following stage d'), which is followed by stage e):

d') adsorption of the active components to a poly-styrene-based adsorption resin; flushing the resin with water; elution of the active constituents with ethanol.

In accordance with this modification, a typical extract of the invention can be produced by adsorption of the active components (isoflavones and saponins), which are present in the concentrated alcohol extract of the plant material, to a polystyrene-based adsorption resin such as duolite or any XAD, in particular XAD1180 owing to its slightly acidic pH; and elution of the mixture of isoflavones and group B soya saponins in turn with ethanol after careful flushing of the resin column with water to remove salts and other inactive components.

The extract obtained under these conditions contains 13 to 17% by weight of isoflavones and 0.6 to 1.5 parts by weight of group B soya saponins, depending on the quality of the plant material used, per 1 part by weight of glucoside isoflavones. This extract also contains a large amount of polyphenolic substances which proved to be essential for the inherent activity of the extract.

An embodiment of the abovementioned process and its modification comprises the following stages:
f) suspending the extract from stage e) in a mixture of a water-miscible alcohol and water and diluting it with a water-immiscible aprotic solvent;
g) heating the mixture from stage f) to complete the dissolution and leaving it at room temperature;
h) collecting the precipitated group B soya saponins by filtration;
i) separating off the organic phase from the water phase; and concentrating the organic phase and drying it to produce the isoflavone components; and
j) mixing the saponins from stage h) and the isoflavones from stage i) in order to form the extract.

Therefore, the extracts according to the invention can preferably, even those which are characterized by a very high content of glucoside isoflavones and group B soya saponins in the above-described ratio, also be produced from the extract obtained in accordance with the above-described process or its modification. For this purpose, the procedure can be followed as follows: the said extract is suspended in a water-miscible alcohol, such as ethanol or methanol, having a water content of 10 to 50% by volume, and diluted with a water-immiscible aprotic solvent, such as methylene chloride or ethyl acetate. The heterogeneous mixture obtained is heated to complete the dissolution of the extract and left at room temperature, so that the group B soya saponins can precipitate out. The saponins which have a purity of over 90% are collected by filtration. The isoflavone components which have a purity of more than 80% are obtained from the aqueous mother liquor by separating off the organic phase and evaporating and drying the latter. The isoflavones and saponins can then be mixed in order to obtain an extract having a highest possible content of glucoside isoflavones and having a group B soya saponin content of 0.6 to 1.5 parts by weight per 1 part by weight of glucoside isoflavones.

Preferred conditions for carrying out the individual process stages of the process according to the invention are as follows. In this case the units of measurement for parts by volume are 1 (liters) and those for parts by weight are kg (kilograms).

Stage a: The plant material is preferably extracted with 12 to 17 volumes of solvent per 1 part (weight) of biomass. The extraction temperature is expediently above 55° C. Each extraction is expediently carried out in the course of less than 4 hours. Suitable solvents in addition to ethanol are, inter alia, methanol, propanol and isopropanol. These solvents can contain water up to 10%.

Stage b: The extract is expediently concentrated at a temperature below 50° C. under reduced pressure. The extract is expediently concentrated to an alcohol content of 65 to 75%.

Stage c: The purification is expediently performed using 0.3 to 0.6 volumes of aliphatic hydrocarbons per 1 part (by weight) of plant material. A suitable procedure is that of extracting the oily and lipophilic substances.

Stage d: The active compounds are expediently extracted with 0.2 to 0.4 volumes of alcoholic water-immiscible solvent per extraction, calculated on 1 part (by weight) of plant material; preferably, three extractions are carried out.

Stage e: The extract from stage d is expediently concentrated at a temperature below 50° C. under reduced pressure.

Stage f: The extract from stage e) is expediently suspended in 5 to 10 volumes (per 1 part of extract) of water-soluble alcohol, using an alcohol/water ratio in the range from 2:8 to 3:7 vol/vol. The aprotic water-immiscible solvent is expediently used in an amount of 2 to 5 volumes, based on 1 part (by weight) of the extract from stage e.

Stage g: To achieve complete dissolution, the mixture is expediently heated and kept under reflux. The mixture is then preferably maintained at room temperature for 15 to 24 h.

Stage i: The organic phase is expediently concentrated by evaporation at a temperature of below 30° C. under reduced pressure.

Stage j: Preferably, the saponins from stage h and the glucoside isoflavones from stage g are used to prepare an alcoholic solution which contains the saponins and glucoside isoflavones in a ratio of 1:1, which solution is then expediently concentrated to dryness at a temperature below 50° C. under reduced pressure.

The amounts of the isoflavones and the group B soya saponins are determined by EPLC analysis using a Supelco-Sil LC-ABZ column (250 mm×4.6 mm), 5 $\mu$m, and a ternary elution medium using a gradient, comprising A) $H_2O$ ($CF_3COOH$ 0.01%), B) acetonitrile ($CF_3COOH$ 0.01%) and C) methyl alcohol ($CF_3COOH$ 0.01%). The individual components can be identified and characterized by mass spectrometry combined with HPLC via a thermospray interface.

The extracts according to the invention are distinguished from previously known extracts with respect to their special action.

With respect to menopause disorders, hot flushes, sleeplessness and depression are the most frequent climacteric symptoms from which women suffer during menopause. They are accompanied by a decrease or cessation in ovarian activity and therefore by decreased oestrogen production and increased production of luteinizing hormone (LH) and follicle-stimulating hormone (FSH).

A recent study (Duker E. M. et al.; Planta. med. 57, 420, 1991) reported an association between an occasional increase in LH and temperature changes in the skin of female rats following an ovariotomy. This relationship between LH level and hot flushes, which has been observed not only in the case of female rats but also with women, suggests that the dose of secreted LH can be considered as a suitable parameter for the study of psychoneurotic/endocrine effects of active endocrine compounds.

Table 1 shows the results which were obtained when ovariectomized female rats were treated with two separate fractions (isoflavones and group B soya saponins) and the extracts according to the invention.

TABLE 1

Concentration of luteinizing hormone (LH) in the plasma of ovariectomized female rats after oral treatment with soya extracts

| Product administered | Dose (mg/kg/day) | LH (ng/ml) |
| --- | --- | --- |
| Vehicle | 10 ml/kg | 6.2 ± 0.01 |
| Group B soya saponins | 1,000 | 5.8 ± 0.02 |
| Soya isoflavones | 1,000 | 3.4 ± 0.001 |
| Soya extract prepared as in Example 1 | 1,000 | 2.1 ± 0.001 |
| Soya extract prepared as in Example 3 | 1,000 | 1.3 ± 0.001 |

The female rats were subjected to ovariotomy by known methods. 15 days after the operation the animals were treated with the test substances by single oral administration per day for 15 days. The animals were killed 3 hours after the last treatment. The blood was centrifuged immediately thereafter and the serum obtained was stored at −25° C. until determination of LH by radioimmunoassay in accordance with the method described by Niswender et al. (Proc. Soc. Exp. Biol. Med. 128, 807, 1986).

As can be seen, administering the extracts according to the invention led to a statistically significant decrease in LH, which was greater than that obtained for the sum of the individual components (synergistic effect).

The extracts employed in repeated treatments of healthy animals led to no macroscopic or microscopic changes in the organs or systems of male animals, whereas in the female animals they modify the weight of uterus and skeleton, which confirms their oestrogenic activity.

When the extracts according to the invention were administered to women during menopause—regardless of whether this occurred naturally or was caused surgically—they modified the plasma LH level and reduced menopausal disorders such as hot flushes or depression etc. within a few days of treatment, and also reduced bone demineralization during treatment over longer periods.

The extracts according to the invention also have marked anitproliferative activity. Table 2 shows the antiproliferative activity towards on ovarian tumour cell line (OVCA 433).

TABLE 2

Antiproliferative activity of soya extracts towards an ovarian tumour cell line (OVCA 433) in vitro.

| Compound | $IC_{50}$ $\mu$M |
| --- | --- |
| Group B soya saponins | 6.2 |
| Soya isoflavones | 4.5 |
| Soya extract prepared as in Example 1 | 1.6 |
| Soya extract prepared as in Example 3 | 1.1 |

The cells were cultured in a monolayer culture on a minimum of essential medium containing added calf serum and 200 units/ml of penicillin to keep the medium sterile. For reproducibility of the tests, the cells were trypsinized each week and applied to plates at a density of $8 \times 10^4$ cells/ml and incubated at 37° C. under an air atmosphere at a content of 5% $CO_2$ and moisture. To assay the activity of the compounds, the cells were placed in wells (Falcon 3046, Becton Dickinson NY) at a concentration of $1 \times 10^5$/ml in a minimal amount of substrate. After 24 h, the substrate was replaced by fresh substrate and the compounds dissolved in absolute ethanol were added. Controls were treated similarly with the excipient in the absence of the active compound to be tested. The above described treatment was repeated at intervals of 24 hours for a test period of 72 h. The inhibition of cell proliferation was assessed by direct enumeration of the cells, with the growth of the controls being compared to that of the "treated" test. As shown, the extracts according to the invention possessed an antiproliferative activity which is greater than the sum of the antiproliferative activity of their components (synergistic activity). The compounds according to the invention inhibited cell proliferation in vivo, as verified by measuring the size of tumours transplanted into naked athymic mice in accordance with the usual conditions reported in the literature. Treating the animals with doses in the range from 10 to 500 mg/kg led to a marked degeneration of the tumours studied, up to their disappearance in a high percentage of the individuals.

As regards the inhibitory effect on alcohol consumption, this effect was determined using alcohol-consuming rats of the species "Sardinian alcohol-preferring" (Sp) (Fadda F., Mosca E., Colombo G., Gessa G. L., *Alcohol preferring rats; Genetic sensitivity to alcohol-induced stimulation of dopamine metabolism*, in Physiol. Behav. 47, 727 (1990)). These animals which, with a free choice between alcohol and water, consume 6 to 7 g of alcohol daily per kg of bodyweight (at a water to alcohol ratio of greater than 2:1) have successfully been used in recent years to determine the effect of various substances on voluntary alcohol consumption, see, for example, Balakleevsky A., Colombo G., Fadda F., Gessa G. L., *Ro 19-4603, a benzodiazepine receptor inverse agonist, attenuates voluntary ethanol consumption in rats selectively bred for high ethanol preference*, in Alcohol Alcohol 25, 449–452 (1990); Fadda F., Garau B., Colombo G., Gessa G. L., *Isradipine and other calcium channel antagonists attenuate ethanol consumption in ethanol-preferring rats*, in Alcoholism: Clinical and Experimental Research 16 (3), 449–452 (1992).

The animals which were kept under normal conditions of accommodation could freely select between water (which was always present) and alcohol (a 10% strength solution vol/vol) which was offered during a period of 4 h per day (i.e. the first four hours of darkness during the day/night cycle). The amounts of water and alcohol consumed were recorded for each day at the same time. Food was offered ad libitum. After a stable alcohol and water consumption was achieved, the extract, at a dose of 1000 mg/kg suspended in water, was administered orally in a volumetric amount of 2 ml/kg once per day for 7 successive days. As a control, an identical volume of excipient was used. At the end of the treatment, the alcohol consumption was recorded until the values before the treatment were achieved.

Table 3 shows the effect of repeated oral administration of 1000 mg/kg of soya extract on the alcohol consumption.

TABLE 3

Effect of the repeated oral administration of soya extracts on alcohol consumption in Sp (Sardinian alcohol-preferring)

| Compound | Dose (mg/kg) | Alcohol consumption (g/kg) | | | | | | | | | |
|---|---|---|---|---|---|---|---|---|---|---|---|
| | | Day 1 | Day 2 | Day 3 | Day 4 | Day 5 | Day 6 | Day 7 | Day 8 | Day 9 | Day 10 |
| Vehicle | 2 ml/kg | 2.9 ± 0.1 | 2.9 ± 0.2 | 2.8 ± 0.3 | 2.9 ± 0.2 | 2.6 ± 0.2 | 3.0 ± 0.1 | 2.9 ± 0.3 | 2.9 ± 0.1 | 2.8 ± 0.2 | 2.6 ± 0.2 |
| Group B soya saponins | 1000 | 2.8 ± 0.1 | 2.8 ± 0.3 | 2.9 ± 0.2 | 2.7 ± 0.3 | 2.2* ± 0.1 | 2.2* ± 0.1 | 2.6 ± 0.2 | 2.7 ± 0.2 | 2.9 ± 0.1 | 3.0 ± 0.2 |
| Soya isoflavones | 1000 | 2.6 ± 0.2 | 2.9 ± 0.2 | 2.8 ± 0.1 | 2.9 ± 0.3 | 1.9* ± 0.2 | 1.9* ± 0.2 | 2.0* ± 0.1 | 1.9* ± 0.1 | 2.3 ± 0.2 | 2.6 ± 0.3 |
| Soya extract, produced in accordance with Example 1 | 1000 | 3.0 ± 0.2 | 2.9 ± 0.1 | 2.9 ± 0.3 | 2.0* ± 0.1 | 1.8* ± 0.1 | 1.6** ± 0.1 | 1.4** ± 0.2 | 1.5** ± 0.1 | 2.0 ± 0.2 | 2.4 ± 0.3 |
| Soya extract, produced in accordance with Example 3 | 1000 | 2.8 ± 0.2 | 2.9 ± 0.3 | 3.0 ± 0.3 | 2.1* ± 0.1 | 1.6** ± 0.1 | 1.7** ± 0.1 | 1.2** ± 0.2 | 1.2** ± 0.1 | 1.9* ± 0.2 | 2.2 ± 0.3 |

*$p < 0.05$, **$p < 0.01$;
Dunnet's t-test for a multiple comparison versus vehicle-treated animal.

Table 3 leads to the conclusion that soya extract significantly decreases the alcohol consumption. The reduction in alcohol consumption remains constant during the 7 treatment days and then decreases after the end of treatment. Furthermore, it can be seen that the reduction in alcohol consumption is greater than that which is given by the sum of the effects of the individual components (synergistic effect).

The invention therefore also relates to a pharmaceutical composition which contains the above-defined extract as active component. In particular, the invention relates to a pharmaceutical composition containing this extract for the prevention or the treatment of pre-menopausal and post-menopausal symptoms, to a pharmaceutical composition containing this extract for the prevention and treatment of breast cancer in women and of prostate cancer in men and to a pharmaceutical composition containing this extract for the prevention or treatment of alcoholism.

The products or extracts according to the invention can be formulated in a suitable manner in tablets, soft or hard gelatine capsules, granular powders for preparing ready-to-use solutions or fluids or liquids which are compatible with their solubility. The doses of the extract according to the invention are in the range from 30 mg to 500 mg in the case of single or repeated administration per day, preferably 200 mg with administration twice per day. The oral form is the expedient form of administration.

EXAMPLES

The following examples illustrate the invention.

Example 1

Production of Soya Extract Having an Isoflavone Content of 15% by Weight and a Ratio of Glucoside Isoflavones/Group B Soya Saponins of 1:1.5 by Purification with Solvents 10 kg of oil-freed soya flour containing 0.2% of glucoside isoflavones and 0.3% of group B soya saponins are refluxed five times with 30 l of 95% strength ethyl alcohol. The alcohol extracts are mixed and concentrated under reduced pressure to 5 l. The concentrate is diluted with 1.5 l of water and extracted four times with 5 l of n-hexane. The hexane phase is discarded and the concentrate; alcohol phase is extracted four times using 2.5 l of n-butanol. The organic phase is concentrated and dried under reduced pressure. 133 g of extract having an isoflavone content of 15% by weight and a group B soya saponin content of 22.5% by weight are obtained.

An HPLC diagram of an extract obtained by the process of this example is shown in FIG. 1.

Example 2
Production of a Soya Extract Having an Isoflavone Content of 15% by Weight and a Ratio of Glucoside Isoflavones/Group B Soya Saponins of 1:1.5 by Purification on Polystyrene Resin The aqueous concentrate produced in Example 1 is not extracted with n-butanol, but treated with polyethoxylated castor oil (Cremophor®), to dissolve the resinous residues from the concentration of the alcohol phase. It is then applied, suspended in purified water (5 l), to a column of XAD1180 resin. The column is then flushed with water for complete removal of salts, sugars and surface-active agents and then eluted with about 10 l of 95% strength ethyl alcohol. After concentrating and drying the ethanol eluate, 130 g of extract having the same composition as that of the extract obtained in Example 1 are obtained.

Example 3
Production of a Soya Extract Having an Isoflavone Content of 43% by Weight and a Ratio of Glucoside Isoflavones/Group B Soya Saponins of 1:1

200 g of the extract obtained in Example 1 or 2 are suspended in 1 l of aqueous 20% strength ethyl alcohol and diluted with 0.5 l of ethyl acetate. The suspension is subjected to a countercurrent heating with vigorous stirring until complete dissolution and then left for the course of one night. The saponins precipitated out (38 g, purity 93%) are isolated by filtration and the ethylacetate- and water-containing aqueous mother liquor is separated off. The organic phase is concentrated under reduced pressure and dried. The isoflavone residue—37 g having a purity of 81%—is dissolved in 1 l of ethyl alcohol and admixed with 32 g of crystallized saponins, in order to obtain a product which contains isoflavones and saponins in a weight ratio of 1:1. The alcoholic solution is concentrated to dryness under reduced pressure and gives 69 g of extract having a content of 43% by weight of glucoside isoflavones and 43% by weight of group B soya saponins.

Example 4
Production of Hard Gelatine Capsules Containing Soya Extract

| | |
|---|---|
| Soya extract produced in accordance with Example 1 | 200.0 mg |
| Lactose | 67.5 mg |
| Microcrystalline cellulose | 22.5 mg |
| Colloidal silicon dioxide | 3.0 mg |
| Croscarmellose sodium (crosslinked polymer of carboxymethylcellulose sodium) | 21.0 mg |
| Talc | 8.0 mg |
| Magnesium stearate | 3.0 mg |

Example 5
Production of Tablets Containing Soya Extract

| | |
|---|---|
| Soya extract, produced in accordance with Example 3 | 400.0 mg |
| Soya polysaccharides | 155.5 mg |
| Microcrystalline cellulose | 57.0 mg |
| Hydroxypropylmethylcellulose | 12.0 mg |
| Hydrogenated vegetable oil | 19.5 mg |
| Colloidal silicon dioxide | 3.0 mg |
| Magnesium stearate | 3.0 mg |

Example 6

The following table shows further results obtained when ovariectomized femal rats were treated with the below extracts A, B, C and D. The test method is that as described in the present application.

Extract A: weight ratio of isoflavones to saponins of 1:0.5;
Extract B: weight ratio of isoflavones to saponins of 1:2;
Extract C: weight ratio of isoflavones to saponins of 1:1;
Extract D: weight ratio of isoflavones to saponins of 1:1.5.

The extracts A to C were obtained according to the method of example 3; extract D corresponds to the extract of example 1.

TABLE

Concentration of luteinizing hormone (LH) in the plasma ovariectomized female rats after oral treatment with soya extracts

| Product administered | Dose (mg/kg/day) | LH (ng/ml) |
|---|---|---|
| Vehicle | 10 ml/kg | 7.4 ± 0.03 |
| Extract A (comparison) | 1000 | 5.1 ± 0.02 |
| Extract B (comparison) | 1000 | 6.7 ± 0.01 |
| Extract C | 1000 | 2.96 ± 0.002 |
| Extract D | 1000 | 2.13 ± 0.001 |

Example 7

The following table is directed to further results concerning the antiproliferative activity towards an ovarian tumour cell line in vitro obtained for the following extracts A to D:

Extract A: weight ratio of isoflavones to saponins of 1:0.5;
Extract B: weight ratio of isoflavones to saponins of 1:2;
Extract C: weight ratio of isoflavones to saponins of 1:1;
Extract D: weight ratio of isoflavones to saponins of 1:1.5.

The extracts A to C were obtained according to the method of example 3 of the invention; extract D corresponds to the extract of example 1 thereof. The test method is that as described in the present application.

TABLE

Antiproliferative activity of soya extracts towards an ovarian tumour cell line (OVCA 433) in vitro.

| Compound | $IC_{50}\ \mu M$ |
|---|---|
| Extract A (comparison) | 4.2 |
| Extract B (comparison) | 5.3 |
| Extract C | 1.4 |
| Extract D | 1.2 |

Example 8

The following table shows further results for the effect of the repeated oral administration on alcohol consumption for the following extracts A and B:

Extract A: weight ratio of isoflavones to saponins of 1:0.5;
Extract B: weight ratio of isoflavones to saponins of 1:2.

The extracts A and B were obtained according to the method of example 3 of the present invention; the test method is that as described in the present application.

TABLE

Effect of the repeated oral administration of soya extracts on alcohol consumption in Sp (Sardinian alcohol preferring)

| Compound | Dose (mg/kg) | Alcohol consumption (g/kg) | | | | | | | | | |
|---|---|---|---|---|---|---|---|---|---|---|---|
| | | Day 1 | Day 2 | Day 3 | Day 4 | Day 5 | Day 6 | Day 7 | Day 8 | Day 9 | Day 10 |
| Vehicle | 2 ml/kg | 2.7 ± 0.2 | 2.9 ± 0.1 | 2.8 ± 0.3 | 2.9 ± 0.2 | 2.7 ± 0.1 | 2.8 ± 0.2 | 2.9 ± 0.2 | 2.9 ± 0.1 | 2.9 ± 0.3 | 2.8 ± 0.2 |
| Extract A (1:0.5) (comparison) | 1000 | 2.9 ± 0.1 | 2.9 ± 0.3 | 2.8 ± 0.2 | 2.7 ± 0.1 | 2.7 ± 0.3 | 2.6 ± 0.2 | 2.6 ± 0.1 | 2.5 ± 0.3 | 2.6 ± 0.2 | 2.8 ± 0.4 |
| Extract B (1:2) (comparison) | 1000 | 2.8 ± 0.2 | 2.8 ± 0.1 | 2.9 ± 0.1 | 2.7 ± 0.2 | 2.6 ± 0.1 | 2.5 ± 0.3 | 2.6 ± 0.1 | 2.7 ± 0.3 | 2.7 ± 0.2 | 2.8 ± 0.1 |

Dunnet's t-test for a multiple comparison versus vehicle-treated animal

What is claimed is:

1. A soya extract having a content of glucoside isoflavones of at least 13% by weight and a content of 0.6 to 1.5 parts by weight of group B soya saponins per 1 part by weight of glucoside isoflavones.

2. The soya extract of claim 1, wherein the content of group B soya saponins is 1 part by weight per 1 part by weight of glucoside isoflavones.

3. A pharmaceutical composition containing, as an active component, the soya extract of claim 1 and a pharmaceutically acceptable carrier or diluent.

4. A pharmaceutical composition containing, as an active component, the soya extract of claim 2 and a pharmaceutically acceptable carrier or diluent.

* * * * *

UNITED STATES PATENT AND TRADEMARK OFFICE
CERTIFICATE OF CORRECTION

PATENT NO. : 6,607,757 B2
DATED : August 19, 2003
INVENTOR(S) : Ezio Bombardelli and Bruno Gabetta It is certified that error appears in the above-identified patent and that said Letters Patent is hereby corrected as shown below:

<u>Title page,</u>
Item [75], Inventors, replace each occurrence of "Milan" with -- Milano --.
Item [73], Assignee, replace "Milan" with -- Milano --.

Signed and Sealed this

Eleventh Day of November, 2003

JAMES E. ROGAN
*Director of the United States Patent and Trademark Office*